US008758374B2

(12) United States Patent
Agarwal

(10) Patent No.: US 8,758,374 B2
(45) Date of Patent: Jun. 24, 2014

(54) METHOD FOR CONNECTING NERVES VIA A SIDE-TO-SIDE EPINEURIAL WINDOW USING ARTIFICIAL CONDUITS

(75) Inventor: Jayant P. Agarwal, Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 102 days.

(21) Appl. No.: 13/200,028

(22) Filed: Sep. 15, 2011

(65) Prior Publication Data

US 2012/0065740 A1 Mar. 15, 2012

Related U.S. Application Data

(60) Provisional application No. 61/403,489, filed on Sep. 15, 2010.

(51) Int. Cl.
*A61F 2/04* (2013.01)
*A61B 17/08* (2006.01)

(52) U.S. Cl.
USPC ...... 606/152; 606/155; 623/23.64; 623/23.71

(58) Field of Classification Search
USPC ............... 623/23.64, 23.65, 23.71, 23.72; 606/151–156
See application file for complete search history.

(56) References Cited

U.S. PATENT DOCUMENTS

| 4,662,884 A | 5/1987 | Stensaas |
| 4,669,474 A | 6/1987 | Barrows |
| 4,759,764 A | 7/1988 | Fawcett et al. |
| 4,774,967 A | 10/1988 | Zanakis et al. |
| 4,778,467 A | 10/1988 | Stensaas et al. |
| 4,870,966 A | 10/1989 | Dellon et al. |
| 4,883,618 A | 11/1989 | Barrows |
| 4,963,146 A | 10/1990 | Li |
| 4,986,828 A | 1/1991 | de Medinaceli |
| 5,019,087 A | 5/1991 | Nichols |
| 5,354,305 A | 10/1994 | Lewis, Jr. et al. |
| 5,376,662 A | 12/1994 | Ockert |
| 5,770,417 A | 6/1998 | Vacanti et al. |
| 6,309,635 B1 | 10/2001 | Ingber et al. |
| 6,448,076 B2 | 9/2002 | Dennis et al. |
| 6,514,515 B1 | 2/2003 | Williams |

(Continued)

FOREIGN PATENT DOCUMENTS

| AU | 2006329152 | 1/2012 |
| CA | 2078982 | 5/1999 |

(Continued)

OTHER PUBLICATIONS

Chen, Z., et al., "Comparison of the nerve regeneration of end-to-side neurorrhaphy and side-to-side neurorrhaphy: an experimental study", Chinese Journal of Practical Hand Surgery. Mar. 2001.

(Continued)

*Primary Examiner* — David Isabella
*Assistant Examiner* — Yashita Sharma
(74) *Attorney, Agent, or Firm* — Workman Nydegger

(57) ABSTRACT

The disclosure provides methods for repairing nerves and inhibiting atrophy of a muscle via a side-to side neurorraphy using a bridging element between a first epineurial window on a donor nerve and a second epineurial window on a recipient nerve.

19 Claims, 5 Drawing Sheets
(3 of 5 Drawing Sheet(s) Filed in Color)

(56) References Cited

U.S. PATENT DOCUMENTS

| | | | |
|---|---|---|---|
| 6,548,569 | B1 | 4/2003 | Williams et al. |
| 6,676,675 | B2 | 1/2004 | Mallapragada et al. |
| 6,716,225 | B2 | 4/2004 | Li et al. |
| 6,821,946 | B2 | 11/2004 | Goldspink et al. |
| 6,838,493 | B2 | 1/2005 | Williams et al. |
| 6,840,962 | B1 | 1/2005 | Vacanti et al. |
| 6,867,247 | B2 | 3/2005 | Williams et al. |
| 6,899,873 | B2 | 5/2005 | Ma et al. |
| 6,953,482 | B2 | 10/2005 | Doi et al. |
| 7,135,040 | B2 | 11/2006 | Wang et al. |
| 7,179,883 | B2 | 2/2007 | Williams et al. |
| 7,198,799 | B2 | 4/2007 | Mueller et al. |
| 7,268,205 | B2 | 9/2007 | Williams et al. |
| 7,553,923 | B2 | 6/2009 | Williams et al. |
| 7,615,063 | B2 | 11/2009 | Doi et al. |
| 7,618,653 | B2 | 11/2009 | Xu |
| 7,785,628 | B2 | 8/2010 | Hissink et al. |
| 2002/0086047 | A1 | 7/2002 | Mueller et al. |
| 2002/0156150 | A1 | 10/2002 | Williams et al. |
| 2002/0173558 | A1 | 11/2002 | Williams et al. |
| 2003/0060836 | A1 | 3/2003 | Wang et al. |
| 2003/0072749 | A1 | 4/2003 | Muir |
| 2004/0122454 | A1 | 6/2004 | Wang et al. |
| 2004/0234576 | A1 | 11/2004 | Martin et al. |
| 2005/0069525 | A1 | 3/2005 | Mikael |
| 2006/0018947 | A1 | 1/2006 | Mueller et al. |
| 2007/0067883 | A1 | 3/2007 | Sretavan |
| 2007/0135929 | A1 | 6/2007 | Williams et al. |
| 2007/0141166 | A1 | 6/2007 | Xu |
| 2007/0182041 | A1 | 8/2007 | Rizk et al. |
| 2008/0051490 | A1 | 2/2008 | Williams et al. |
| 2008/0095823 | A1 | 4/2008 | Williams et al. |
| 2008/0132602 | A1 | 6/2008 | Rizk et al. |
| 2009/0024150 | A1 | 1/2009 | Ahlers et al. |
| 2009/0099580 | A1 | 4/2009 | Priestly et al. |
| 2010/0047310 | A1 | 2/2010 | Chen et al. |
| 2010/0055148 | A1 | 3/2010 | Xu |
| 2010/0076465 | A1 | 3/2010 | Wiberg et al. |
| 2010/0094318 | A1 | 4/2010 | Li et al. |
| 2010/0168625 | A1 | 7/2010 | Swain |
| 2010/0168720 | A1 | 7/2010 | Swain et al. |
| 2010/0168870 | A1 | 7/2010 | Swain et al. |
| 2010/0291180 | A1 | 11/2010 | Uhrich |
| 2011/0087338 | A1* | 4/2011 | Siemionow et al. ........ 623/23.72 |
| 2011/0125170 | A1 | 5/2011 | Hoke et al. |
| 2011/0152898 | A1* | 6/2011 | Kochevar et al. ............ 606/152 |

FOREIGN PATENT DOCUMENTS

| | | |
|---|---|---|
| CA | 2634351 | 6/2007 |
| CA | 2713214 | 7/2009 |
| CN | 1380115 | 11/2002 |
| CN | 1843307 | 10/2006 |
| CN | 101138656 | 3/2008 |
| CN | 100479785 | 4/2009 |
| CN | 201230913 | 5/2009 |
| CN | 101474423 | 7/2009 |
| CN | 101474424 | 7/2009 |
| CN | 101507842 | 8/2009 |
| CN | 101543645 | 9/2009 |
| CN | 101564552 | 10/2009 |
| CN | 100560037 | 11/2009 |
| CN | 101579246 | 11/2009 |
| CN | 101711893 | 5/2010 |
| EP | 1650224 | 4/2006 |
| EP | 1878451 | 1/2008 |
| KR | 20030087196 | 11/2003 |
| KR | 20060006295 | 1/2006 |
| KR | 100700674 | 3/2006 |
| KR | 20060018752 | 3/2006 |
| KR | 100718073 | 5/2007 |
| KR | 20090064617 | 6/2009 |
| MX | 2008006463 | 3/2009 |
| TW | 287459 | 10/2004 |
| UA | 9421 | 9/2005 |
| WO | WO 88/06866 | 9/1988 |
| WO | WO 00/51662 | 11/2001 |
| WO | WO 02/47557 | 6/2002 |
| WO | WO 00/56376 | 7/2002 |
| WO | WO 2004/101002 | 11/2004 |
| WO | WO 2005/020825 | 3/2005 |
| WO | WO 2005/037070 | 4/2005 |
| WO | WO 2007/057177 | 5/2007 |
| WO | WO 2007/071167 | 6/2007 |
| WO | WO 2007/092417 | 8/2007 |
| WO | WO 2007/142579 | 12/2007 |
| WO | WO 2008/070428 | 6/2008 |
| WO | WO 2008/121331 | 10/2008 |
| WO | WO 2008/140413 | 11/2008 |
| WO | WO 2008/144514 | 11/2008 |
| WO | WO 2009/085823 | 7/2009 |
| WO | WO 2009/094225 | 7/2009 |
| WO | WO 2009/117127 | 9/2009 |
| WO | WO 2010/042207 | 4/2010 |

OTHER PUBLICATIONS

Alluin, O. et al., "Functional recovery after peripheral nerve injury and implantation of a collagen guide" Biomaterials. Jan. 2009;30(3):363-73.

Amr, S.M., et al., "Direct cord implantation in brachial plexus avulsions: revised technique using a single stage combined anterior (first) posterior (second) approach and end-to side side-to-side grafting neurorrhaphy" J Brachial Plex Peripher Nerve Inj. Jun. 2009;4:8.

Amr, S.M., et al., "Repair of brachial plexus lesions by end-to-side side-to side grafting neurorrhaphy: experience based on 11 cases" Microsurgery. 2005;25(2):126-46.

Arai, T. et al., "Side-to-side neurorrhaphy in sciatic nerves of rat" J Japanese Soc Surg Hand. 2001;18(2):155-158.

Archibald, S.J., et al. "A collagen-based nerve guide conduit for peripheral nerve repair: an electrophysiological study of nerve regeneration in rodents and nonhuman primates" J Comp Neurol. Apr. 1991;306(4):685-696.

Archibald, S.J., et al., "Factors that influence peripheral nerve regeneration: electrophysiological study of the monkey median nerve" Ann Neurol. 2002;51(1):69-81.

Archibald, S.J., et al., "Monkey median nerve repaired by nerve graft or collagen nerve guide tube" J. Neurosci. 1995;15(5):4109-4123.

Bain, J.R., et al. "Functional evaluation of complete sciatic, peroneal, and posterior tibial nerve lesions in the rat" Plast Reconstr Surg. 1989;83:129-138.

Benito-Ruiz, J., et al., "Invaginated vein graft as nerve conduit: an experimental study" Microsurgery. 1994;15(2):105-15.

Berger, A. et al., [The Dellon tube in injuries of peripheral nerves]. Handchir Mikrochir Plast Chir. Jan. 1994;26(1):44-7.

Bertleff, M.J., et al., "A prospective clinical evaluation of biodegradable neurolac nerve guides for sensory nerve repair in the hand" J Hand Surg Am. May 2005;30(3):513-8.

Biers, S.M., et al., "Nerve regeneration: might this be the only solution for functional problems of the urinary tract?" Curr Opin Urol. Nov. 2003;13(6):495-500.

Burnett, M.G., et al., Pathophysiology of peripheral nerve injury: a brief review. Neurosurg Focus. May 2004;16(5):E1.

Chen, Z., et al., "Comparison of the nerve regeneration of end-to-side neurorrhaphy and side-to-side neurorrhaphy: an experimental study" Chinese Journal of Practical Hand Surgery. Jan. 2001.

Clavijo-Alvarez, J.A., et al., "Comparison of biodegradable conduits within aged rat sciatic nerve defects" Plast Reconstr Surg. May 2007;119(6):1839-1851.

Cui, T., et al., "Rapid prototyping of a double-layer polyurethane-collagen conduit for peripheral nerve regeneration" Tissue Eng Part C Methods. Mar. 2009;15(1):1-9.

de Ruiter, G.C., et al., "Designing ideal conduits for peripheral nerve repair" Neurosurg Focus. Feb. 2009;26(2):E5.

Deumens, R., et al., Repairing injured peripheral nerves: Bridging the gap. Prog Neurobiol. Nov. 2010;92(3):245-76.

Fabre, T., et al., "Study of a (trimethylenecarbonate-co-epsilon-caprolactone) polymer—part 2: in vitro cytocompatibility analysis and in vivo ED1 cell response of a new nerve guide" Biomaterials. Nov. 2001;22(22):2951-8.

(56) References Cited

OTHER PUBLICATIONS

Gatta, R., "Sulla anastomosi latero-terminale dei tronchi nervosa" Archivio Italiano Chirurgia. 1938;48:155-171.
Hayashi, A., et al., "Axotomy or compression is required for axonal sprouting following end-to-side neurorrhaphy" Exp Neurol. Jun. 2008;211(2):539-50.
Hobson, M.I., "Increased vascularisation enhances axonal regeneration within an acellular nerve conduit" Ann R Coll Surg Engl. Jan. 2002;84(1):47-53.
Ichihara, S., "Development of new nerve guide tube for repair of long nerve defects" Tissue Eng Part C Methods. Sep. 2009;15(3):387-402.
Itoh, S., et al., "Evaluation of cross-linking procedures of collagen tubes used in peripheral nerve repair" Biomaterials. Dec. 2002;23(23):4475-81.
Jansen, K., et al., "Long-term regeneration of the rat sciatic nerve through a biodegradable poly(DL-lactide epsilon-caprolactone) nerve guide: tissue reactions with focus on collagen III/IV reformation" J Biomed Mater Res A. May 2004;69(2):334-41.
Jansen, K., et al., "Long-term regeneration of the rat sciatic nerve through a biodegradable poly(DL-lactide-epsiloncaprolactone) nerve guide: tissue reactions with focus on collagen III/IV reformation [Erratum]" J Biomed Mater Res A. May 2006;77(2):436.
Jansen, K., et al. "A hyaluronan-based nerve guide: in vitro cytotoxicity, subcutaneous tissue reactions, and degradation in the rat" Biomaterials. Feb. 2004;25(3):483-9.
Jeans, L..A., et al., "Peripheral nerve repair by means of a flexible biodegradable glass fibre wrap: a comparison with microsurgical epineurial repair" J. Plast. Reconstr. Aesthet. Surg. 2007;60(12):1302-8.
Jung, J.M., et al., "Contribution of the proximal nerve stump in end-to-end nerve repair: In a rat model" Clin. Orthop. Surg. 2009;1:90-95.
Kalbermatten, D.F., et al., "New fibrin conduit for peripheral nerve repair" J Reconstr Microsurg. Jan. 2009;25(1):27-33.
Kitahara, A.K., et al., "Facial nerve repair accomplished by the interposition of a collagen nerve guide" J Neurosurg. Jul. 2000;93(1):113-20.
Kitahara, A.K., et al., "Facial nerve repair using a collagen conduit in cats" Scand J Plast Reconstr Surg Hand Surg. Jun. 1999;33(2):187-93.
Li, S.T., et al., "Peripheral nerve repair with collagen conduits" Clin Mater. 1992;9(3-4):195-200.
Liu, B.S. "Fabrication and evaluation of a biodegradable proanthocyanidin-crosslinked gelatin conduit in peripheral nerve repair" J Biomed Mater Res A. Dec. 2008;87(4):1092-102.
Ljungberg, C., et al., "Neuronal survival using a resorbable synthetic conduit as an alternative to primary nerve repair" Microsurgery. 1999;19(6):259-264.
Mackinnon, S.E. "Clinical outcome following nerve allograft transplantation" Plast Reconstr Surg. 2001;107:1419-1429.
Mackinnon, S.E., et al., "A primate model for chronic nerve compression" J Reconstr Microsurg. 1985;1:185-194.
Magdi Sherif, M., et al., "Intrinsic hand muscle reinnervation by median-ulnar end-to-side bridge nerve graft: Case report" J Hand Surg. 2010;35A:446-450.
Matsumoto, K., et al., "Peripheral nerve regeneration across an 80-mm gap bridged by a polyglycolic acid (PGA)-collagen tube filled with laminin-coated collagen fibers: a histological and electrophysiological evaluation of regenerated nerves" Brain Res. Jun. 2000;868(2):315-28.
Meek, M.F., et al., "US Food and Drug Administration/Conformit Europe-approved absorbable nerve conduits for clinical repair of peripheral and cranial nerves" Ann Plast Surg. Apr. 2008;60(4):466-72.
Meek, M.F., et al., "Secondary digital nerve repair in the foot with resorbable p(DLLA-epsilon-CL) nerve conduits" J Reconstr Microsurg. Apr. 2006;22(3): 149-51.
Meyer, R.S., et al., "Functional recovery following neurorrhaphy of the rat sciatic nerve by epineurial repair compared with tubulization" J Orthop Res. Sep. 1997;15(5):664-9.
Myckatyn et al., "Microsurgical Repair of Peripheral Nerves and Nerve Grafts," Grabb and Smith's Plastic Surgery, 6th Ed. (2007).
Navarro, X., et al., "Engineering an artificial nerve graft for the repair of severe nerve injuries" Med Biol Eng Comput. Mar. 2003;41(2):220-6.
Nectow, A., et al., "Biomaterials for the development of peripheral nerve guidance conduits" Tissue Eng Part B Rev. Aug. 2011.
Okamoto, H., et al., "Recovery process of sciatic nerve defect with novel bioabsorbable collagen tubes packed with collagen filaments in dogs" J Biomed Mater Res A. Mar. 2010;92(3):859-68.
O'Neill, A.C., et al., "Preparation and integration of human amnion nerve conduits using a light-activated technique" Plast Reconstr Surg. Aug. 2009;124(2):428-37.
Papalia, I., et al., "Origin and history of end-to-side neurorrhaphy. Microsurgery. 2007;27(1):56-61.
Patel, M., et al., "GDNF-chitosan blended nerve guides: a functional study" J Tissue Eng Regen Med. Sep.-Oct. 2007;1(5):360-7.
Patel, M., et al., "Collagen-chitosan nerve guides for peripheral nerve repair: a histomorphometric study" J Biomater Appl. Sep. 2008;23(2):101-21.
Ray, W.Z., et al., "Management of nerve gaps: Autografts, allografts, nerve transfers, and end-to-side neurorrhaphy" Exp Neurol. May 2010;223(1):77-85.
Smith, R.M., et al., "Role of small intestine submucosa (SIS) as a nerve conduit: preliminary report" J Invest Surg. Nov.-Dec. 2004;17(6):339-44.
Spyropoulou, G.A., et al., "New pure motor nerve experimental model for the comparative study between end-to-end and end-to-side neurorrhaphy in free muscle flap neurotization" J Reconstr Microsurg. 2007;23(7):391-398.
Stevenson, T.R., et al., "Tubular nerve guide and epineurial repair: comparison of techniques for neurorrhaphy" J Reconstr Microsurg. May 1994;10(3):171-4.
Sun, M., et al., "Novel thin-walled nerve conduit with microgrooved surface patterns for enhanced peripheral nerve repair" J Mater Sci Mater Med. Oct. 2010;21(10):2765-74.
Taras, J.S., et al., "Repair of lacerated peripheral nerves with nerve conduits" Tech Hand Up Extrem Surg. Jun. 2008;12(2):100-6.
Taras, J.S., et al., "Nerve conduits" J Hand Ther. Apr.-Jun. 2005;18(2):191-7.
Teman, C.J., et al., "Quantification of fibrosis and osteosclerosis in myeloproliferative neoplasms: a computer-assisted image study" Leuk Res. 2010;34:871-876.
Terzis, J.K., et al., "The "Babysitter" procedure. minihypoglossal to facial nerve transfer and cross-facial nerve grafting" Plas Reconstr Surg. 2009;123(3):865-876.
Tham, S.K., et al., "Motor collateral sprouting through an end-to-side nerve repair" J Hand Surg. Sep. 1998;23(5):844-851.
Ulkur, E., et al., "Nerve graft prefabrication: preliminary study" J Reconstr Microsurg. Apr. 2008;24(2):137-135.
Vasconcelos, B.C., et al., "Facial nerve repair with expanded polytetrafluoroethylene and collagen conduits: an experimental study in the rabbit" J Oral Maxillofac Surg. Nov. 2000;58(11):1257-62.
Viterbo, F., et al. "End-to-side Neurorrhaphy with removal of the epineurial sheath: an experimental study in rats" Plast Reconstr Surg. Dec. 1994;94(7):1038-1047.
Wangensteen, K.J., et al., "Collagen tube conduits in peripheral nerve repair: A retrospective analysis" Hand (N Y). Nov. 24, 2009.
Watanabe. K., et al., "Nerve conduit using fascia-wrapped fibrocollagenous tube" J Reconstr Microsurg. Jul. 2001;17(5):363-8.
Whitworth, I.H., et al., "Orientated mats of fibronectin as a conduit material for use in peripheral nerve repair" J Hand Surg Br. Aug. 1995;20(4):429-36.
Xiu, X.L., et al., "An experimental study of the side-to-side neurorrhaphy to repair incomplete injury of peripheral nerve" The Orthopedic Journal of China. Oct. 10, 2001.
Yang, Y.C., et al. "Characteristics and biocompatibility of a biodegradable genipin-cross-linked gelatin/betatricalcium phosphate reinforced nerve guide conduit" J Biomed Mater Res B Appl Biomater. Oct. 2010;95(1):207-17.

(56) References Cited

OTHER PUBLICATIONS

Yao, L., et al., "Controlling dispersion of axonal regeneration using a multichannel collagen nerve conduit" Biomaterials. Aug. 2010;31(22):5789-97.

Yoshitatsu, S., et al., Muscle flap mass preservation by sensory reinnervation with end-to-side neurorrhaphy: an experimental study in rats. J Reconstr Microsurg. Sep. 2008;24(7):479-487.

Yuksel, F., et al., "Nerve regeneration through side-to-side neurorrhaphy sites in a rat model: a new concept in peripheral nerve surgery" Plast Reconstr Surg. Dec. 1999;104(7):2092-9.

Yüksel, F., et al., "Two applications of end-to-side nerve neurorrhaphy in severe upper-extremity nerve injuries" Microsurgery. 2004;24(5):363-8.

Yüksel. F., et al., "Nerve regeneration through a healthy peripheral nerve trunk as a nerve conduit: a preliminary study of a new concept in peripheral nerve surgery" Microsurgery. 2002;22(4):138-43.

Zukor, K., et al., "Regenerative medicine: Drawing breath after spinal injury" Nature. 2011;475:177-178.

International Search Report for PCT/US2012/060439 dated Jan. 24, 2013.

Written Opinion for PCT/US2012/060439 dated Jan. 24, 2013.

* cited by examiner

METHOD FOR CONNECTING NERVES VIA A SIDE-TO-SIDE EPINEURIAL WINDOW USING ARTIFICIAL CONDUITS

CROSS-REFERENCE TO RELATED APPLICATIONS

This patent application claims priority to U.S. Provisional Patent Application No. 61/403,489 filed Sep. 15, 2010, the entire content of which is incorporated herein by reference.

BACKGROUND

When a peripheral nerve is severed, the axon segments distal to the injury (i.e. furthest away from the spinal cord) die off in a process called Wallerian degeneration. Current treatment options, such as tension-free primary end-to-end neurorrhaphy and end-to-side (ETS) neurorrhaphy, each suffer from disadvantages. When a nerve is repaired using end-to-end neurorrhaphy, the axons in the proximal segment (closest to the spinal cord) regrow into the denervated distal segment at a rate of about 1 mm per day. Until the axons regrow back into the denervated muscles, the muscles are paralyzed. For nerve injuries where the distance between the distal and proximal ends of the distal segment is great, it may take a long time for the axons to regrow into the denervated muscles. If this process takes too long, the denervated muscles may atrophy. ETS neurorrhaphy is disadvantageous, because the proximal end of the distal segment of the severed nerve must be connected to the side of a donor nerve (e.g., via an epineurial window), and as such, the proximal end of the distal segment cannot be reconnected to the distal end of the proximal segment, and the denervated muscles will never have the opportunity for normal physiologic reinnervation.

SUMMARY OF INVENTION

This disclosure provides methods for repairing nerves and inhibiting atrophy of muscles via a side-to-side neurorrhaphy using bridging elements between epineurial windows.

In some aspects, this disclosure relates to a method for repairing an at least partially transected nerve having proximal and distal segments. The distal segment includes a proximal end and a distal end. The method includes creating a first epineurial window in a side of the distal segment between the proximal and distal ends, and a second epineurial window in a side of a donor nerve. A bridging element is positioned between the first and second epineurial windows. The bridging element has a first end and a second end and defines a conduit. The first end of the bridging element is connected to the first epineurial window and the second end of the bridging element is connected to second epineurial window whereupon the first and second epineurial windows are in fluid communication with each other via the conduit.

In some aspects, this disclosure relates to a method for at least partially inhibiting atrophy of a muscle that has ceased to receive signals from a nerve that has been severed. The method includes creating a first epineurial window in a side of a distal segment of the severed nerve between proximal and distal ends of the distal segment, and a second epineurial window in a side of a donor nerve. A bridging element is positioned between the first and second epineurial windows. The bridging element has a first end and a second end and defines a conduit. The first end of the bridging element is connected to the first epineurial window and the second end of the bridging element is connected to the second epineurial window, whereupon the first and second epineurial windows are in fluid communication with each other via the conduit. The bridging element permits transmission of signals from the donor nerve to the muscle, thereby at least partially inhibiting atrophy of the muscle.

In some aspects, this disclosure relates to a method for repairing peripheral nerve injuries. The method includes performing a side-to-side neurorrhaphy using a bridging element between a first epineurial window on a donor nerve and a second epineurial window on a recipient nerve.

Other aspects of the invention will become apparent by consideration of the detailed description and accompanying drawings.

BRIEF DESCRIPTION OF THE DRAWINGS

The patent or application file contains at least one drawing executed in color. Copies of this patent or patent application publication with color drawings will be provided by the Office upon request and payment of the necessary fee.

DETAILED DESCRIPTION

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein are for the purpose of description and should not be regarded as limiting. The use of "including," "comprising," or "having" and variations thereof herein is meant to encompass the items listed thereafter and equivalents thereof as well as additional items. Unless specified or limited otherwise, the terms "mounted," "connected," "supported," and "coupled" and variations thereof are used broadly and encompass both direct and indirect mountings, connections, supports, and couplings.

Although directional references, such as upper, lower, downward, upward, rearward, bottom, front, rear, etc., may be made herein in describing the drawings, these references are made relative to the drawings (as normally viewed) for convenience. These directions are not intended to be taken literally or limit the present invention in any form. In addition, terms such as "first," "second," and "third" are used herein for purposes of description and are not intended to indicate or imply relative importance or significance.

This disclosure provides methods for repairing at least partially transected or severed peripheral nerves in a manner that at least partially inhibits atrophy of a muscle that has ceased to receive signals from the nerve. The methods include performing side-to-side neurorrhaphy using a bridging element between a first epineurial window on a donor nerve and a second epineurial window on a recipient nerve. Specifically, a bridging element is used to form a conduit between a first epineurial window on a recipient nerve (e.g., the distal segment of a damaged or severed nerve), and a second epineurial window on a donor nerve (e.g., a healthy nerve adjacent to the damaged nerve).

Figure 1:
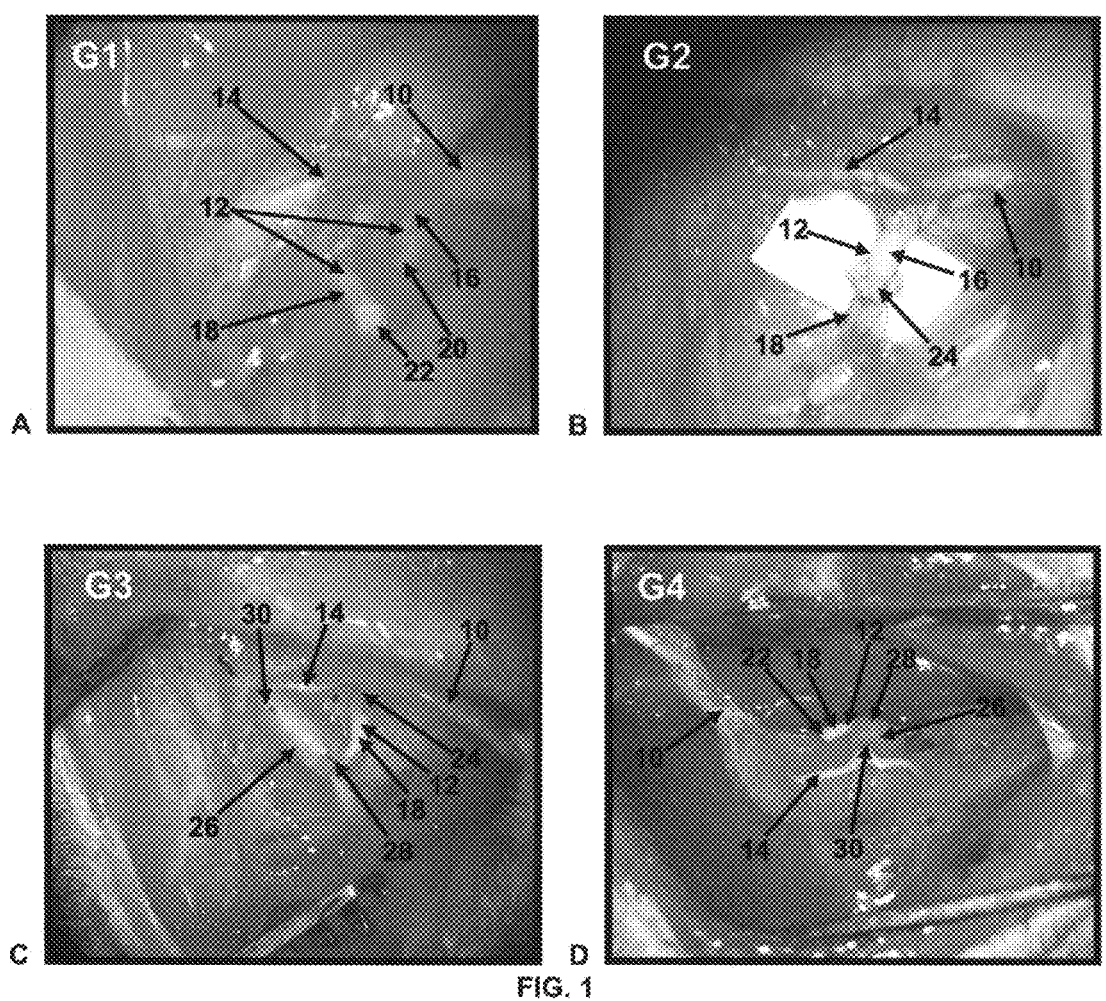
FIG. 1 is a series of photographs showing the sciatic, tibial and peroneal nerves for each of four treatment groups: G1 (FIG. 1A), G2 (FIG. 1B), G3 (FIG. 1C) and G4 (FIG. 1D).

FIG. 1 is a series of photographs showing the arrangement of the sciatic nerve 10, tibial nerve 12 and peroneal nerve 14 for each of four treatment groups (G1, G2, G3, and G4), and are discussed in more detail in the Examples below. Without intending to be limited by any of the particulars shown in FIG. 1, methods of repairing at least partially transected nerves according to this disclosure, which include performing side-to-side neurorrhaphy using a bridging element, are generally discussed herein with reference to FIG. 1.

As shown in FIG. 1A, an at least partially transected nerve, such as tibial nerve 12, includes two segments separated from each other by a site of injury or trauma. The segments include a proximal segment 16 (i.e., the segment closest to the spinal cord) and a distal 18 segment (i.e., the denervated segment furthest from the spinal cord). The proximal segment includes a proximal end (not shown) closest to the spinal cord, and a distal end 20 furthest from the spinal cord. The distal segment includes a proximal end 22 closest to the spinal cord and a distal end (not shown) furthest from the spinal cord. In the case of a completely severed nerve, the distal end of the proximal segment and the proximal end of the distal segment each may be referred to as stump ends.

As shown in FIG. 1B, the proximal segment 16 and distal segment 18 of a severed nerve may be reconnected by performing end-to-end neurorrhaphy. Specifically, the distal end 20 of the proximal segment may be reconnected to the proximal end 22 of the distal segment using a suture 24. However, end-to-end neurorrhaphy has disadvantages discussed above.

Alternatively, the denervated distal segment 18 may be connected to the side of a nearby healthy donor nerve, such as the peroneal nerve 14 shown in FIG. 1. For example, as shown in FIGS. 1C and 1D, side-to-side neurorrhaphy may be performed to connect the side of the denervated distal segment to the side of a nearby healthy donor nerve using a bridging element 26 having a pair of ends and defining a conduit. This process generally may include creating a first epineurial window in the side (i.e., between the proximal and distal ends) of the distal segment, creating a second epineurial window in the side of a donor nerve, positioning the bridging element between the first and second epineurial windows, connecting one end of the bridging element to the first epineurial window to form a first junction 28, and connecting the other end of the bridging element to the second epineurial window to form a second junction 30, whereupon the first and second epineurial windows are in fluid communication with one another via the conduit. In some embodiments, as illustrated by FIG. 1C, end-to-end neurorrhaphy also may be performed to reconnect the distal end 20 of the proximal segment 16 to the proximal end 22 of the distal segment 18 using a suture 24.

The epineurial window on the recipient nerve may be created as close to the denervated muscle as possible to provide early reinnervation of the muscle without donor site morbidity. For example, the epineurial window on the recipient nerve may be substantially proximate to the denervated muscle (i.e., substantially proximate the distal end of the distal segment). In some embodiments, the epineurial window on the recipient nerve may be between about 5-95% of the way between the denervated muscle and the proximal end of the distal segment. In some embodiments, the ideal location for placement of the epineurial window on the recipient nerve is as close to the denervated muscle (i.e., the end organ) as possible. However, there may be practical limitations on the placement of the epineurial window in the recipient nerve, such as the location of the nearest possible donor nerve.

The epineurial windows on the donor nerve and the distal segment of the severed nerve may be the same or different sizes, depending on the size of the donor and/or recipient nerve and the desired size of the bridging element. For example, the size of the epineurial windows may be between about 0.5-5 mm, such as between about 1-4 mm, or between about 1.5-3 mm. The diameter of the bridging element similarly may depend on the desired size of the epineurial window (s). For example, the diameter of the bridging element 10 may be between about 0.5-5 mm, such as between about 1-4 mm, or between about 1.5-3 mm. In particular embodiments, the diameter may be about 1.0, 1.5 or 2.0 mm, among others. The bridging element also may be any suitable length, depending on the width of the gap between the recipient nerve and the donor nerve at a desired position.

The bridging element may be connected to the epineurial windows using any suitable method including, but not limited to, suturing, laser annealing, polymer annealing, or gluing with an adhesive such as cyanoacrylate, fibrin, or thrombin, among others.

The bridging element may include one or more biological materials and/or synthetic materials. Biological materials may include, but are not limited to, autologous biological tissues (e.g., arteries, veins, nerves, muscles, dermis and/or fascia from the subject, among others), non-autologous biological tissues (e.g., allogenic or xenogenic arteries, veins, nerves, muscles, dermis and/or fascia, among others), and conduits manufactured from biologically-derived materials (e.g., fibrous proteins, polysaccharides, and/or glycoproteins, among others). Examples of biologically-derived materials may include, but are not limited to, collagen, fibrin, extracellular matrix solution, fibronectin, alginate, gelatin, keratin, thrombin and silk. Synthetic materials may include, but are not limited to: silicon-containing materials; aliphatic polyesters (e.g., poly-glycolic acid, poly-(lactic acid), poly-caprolactone, poly-(lactide-coglycolide) copolymer, poly-(L-lactic acid) and poly(3-hydroxybutyric acid), among others); polyphosphoesters (e.g., poly((bis(hydroxyethy)terephthalate-ethyl phosphoester/terephthaloyl chloride) and polytetrafluoroethylene, among others); hydrogels (e.g., poly(2-hydroxyethyl methacrylate) (PHEMA) and co-polymers of PHEMA and methyl methacrylate, among others); and poly (acrylonitrile-co-methylacrylate).

In some embodiments, the axons of the donor and/or recipient nerve revealed or otherwise made accessible via the respective epineurial windows may be nicked or otherwise injured prior to connecting the bridging element so as to promote axonal sprouting from the injury. In other embodiments, the bridging element may be connected to the epineurial windows in the donor and recipient nerves without nicking or otherwise injuring the axons of the donor and/or recipient nerves.

As indicated above, upon connecting the bridging element to the epineurial windows on the donor and recipient nerves, the conduit defined by the bridging element causes the epineurial windows to be in fluid communication with each other. The bridging element also permits donor and recipient nerves to be connected side-to-side at virtually any desired location along the length of the distal segment, regardless of whether the distal segment is immediately adjacent the donor nerve. However, prior to performing the experiments described in the Examples below, it was unknown whether a signal could be transmitted from the donor through this side-to-side conduit to the recipient nerve and eventually to the denervated muscle. In fact, it was suspected that chemical and/or electrical signals would not be transmitted through the epineurial window in the side of the donor nerve, through the conduit, and then through an epineurial window in the side of the recipient nerve in a manner that would permit signal transmission to the denervated muscle, in part because the epineurial windows are in the sides of the donor and recipient nerves, and in part because of the gap between the donor and recipient nerves defined by the bridging element. It also was suspected that axons would not grow through the conduit, particularly where (a) the conduit was defined by a manufactured bridging element (as opposed to a nerve graft, which includes biological components, such as Schwann cells, that may support and promote axon growth), and (b) the axons in the donor nerve were not deliberately nicked or injured in a way that would promote axonal growth.

As shown in the Examples below, side-to-side neurorrhaphy using a bridging element between the donor and recipient nerves, according to the various methods disclosed herein, surprisingly and unexpectedly caused signals to be transmitted to a denervated muscle, thereby inhibiting muscle atrophy and preserving muscle mass and motor end-plate viability. Even more surprising was that these signals were transmitted through a synthetic collagen conduit, and axonal growth was observed in the conduit. Further, the axons of the donor nerve were not deliberately injured or nicked in a manner that would stimulate axonal sprouting, and yet axons were still observed growing into the conduit. Growth factors and neurotransmitters also may traverse the bridging element to provide stimulation to the end muscle.

While this disclosure is detailed in terms of a number of aspects and embodiments, variations of those aspects and embodiments may become apparent to those of ordinary skill in the art in light of the foregoing description. The examples that follow are intended merely to be illustrative of certain aspect and embodiments of the disclosure, and should not be interpreted to be limiting to the claims.

EXAMPLES

Example 1

Surgical Procedures 28 male Sprague Dawley rats weighing 350-400 grams were divided into four treatment groups. The rats were anesthetized using Ketamine 50 mg/kg and Xylazine 5 mg/kg via intramuscular injection in the contralateral hind leg. The surgical area was shaved and prepared with betadine. A longitudinal incision was then made in the posterior distal thigh of the hind limb, separating the natural plane between the vertebral head of the biceps femoris and superior gluteal muscles. Under an operative microscope, a 2 cm segment of the sciatic nerve was isolated at its bifurcation into the tibial and peroneal nerves. At this point, the surgical procedure differed between four treatment groups, G1, G2, G3 and G4.

FIG. 1 is a series of photographs showing the arrangement of the sciatic 10, tibial 12 and peroneal 14 nerves for each of four treatment groups: G1 (FIG. 1A), G2 (FIG. 1B), G3 (FIG. 1C) and G4 (FIG. 1D).

Group 1: Transection Only Group (G1)

As shown in FIG. 1A, the tibial nerve 12 was transected to form a proximal segment 16 and a distal segment 18. The resulting stump ends formed by the transaction (i.e., the distal end 20 of the proximal segment and the proximal end 22 of the distal segment) were left unconnected. The incision was then closed with 4-0 suture.

Group 2: Transection and End-to-End Neurorrhaphy (G2)

The tibial nerve 12 was transected to form a proximal segment 16 and a distal segment 18. As shown in FIG. 1B, the distal end of the proximal segment and the proximal end of the distal segment were then sutured back together in an end-to-end fashion with 8-0 nylon suture 24 according to the methods described in Myckatyn and MacKinnon, "Microsurgical Repair of Peripheral Nerves and Nerve Grafts," Grabb and Smith's Plastic Surgery, $6^{th}$ Ed. (2007), the entire disclosure of which is herein incorporated by reference for all purposes. The incision was then closed with 4-0 suture.

Group 3: Transection, End-to-End Neurorrhaphy and Side-to-Side Neurorrhaphy with Collagen Conduit (G3)

The tibial nerve 12 was transected and then sutured back together in an end-to-end fashion with 8-0 nylon suture 24 according to the same methods used for the G2 treatment group. After end-to-end neurorrhaphy was used to repair the tibial nerve, 2 mm epineurial windows were created on the side of the distal segment 18 of the tibial nerve and the side of the nearby peroneal nerve 14 (i.e., the donor nerve), thereby exposing each nerve's axons. As shown in FIG. 1C, a collagen bridging element 26 (i.e., NeuraGen® from Integra Life-Sciences Corp.) having a diameter of about 1.5 mm, and a length of about 0.5 cm, was positioned between the two epineurial windows and was sutured to the epineurium area surrounding the two windows with 11-0 nylon suture, thereby forming junctions 28 and 30. After performing the side-to-side neurorrhaphy, the epineurial windows were in fluid communication with each other via the conduit defined by the bridging element. The incision was then closed with 4-0 suture.

Group 4: Transection and Side-to-Side Neurorrhaphy with Collagen Conduit (G4)

The tibial nerve 12 was transected and left unrepaired. 2 mm epineurial windows were created on the side of the distal segment 18 of the tibial nerve and the side of the nearby peroneal nerve 14 (i.e., the donor nerve), thereby exposing each nerve's axons. As shown in FIG. 1C, a collagen bridging element 26 (i.e., NeuraGen® from Integra LifeSciences Corp.) having a diameter of about 1.5 mm and a length of about 0.5 cm was positioned between the two epineurial windows, and was sutured to the epineurium area surrounding the two windows with 11-0 nylon suture, thereby forming junctions 28 and 30. After performing the side-to-side neurorrhaphy, the epineurial windows were in fluid communication with each other via the conduit defined by the bridging element. The incision was then closed with 4-0 suture.

Post-Operative Treatment of Groups 1-4

All animals were given bacon-flavored Carprofen wafers following surgery for post operative analgesia. The animals were given ad libitum food and water and were checked daily for signs of infection and limb autotomy. The animals' body temperature was monitored during and after surgery, and while the animal recovered from anesthesia. Their body temperature was maintained by use of a heating pad.

Example 2

Tibial Functional Index

The Tibial Functional Index (TFI) is a gait analysis technique to determine the functional status of the tibial nerve in rats. It utilizes paw print measurements of overall paw print length (PL—measured heal to toe), toe spread (TS—distance measured from $1^{st}$ to $5^{th}$ toe), and intermediary toe spread (IT—distance measured from $2^{nd}$ to $4^{th}$ toe). The calculation yields a number from 0 (normal) to −100 (complete tibial nerve lesion). Rats with a tibial nerve lesion express less toe spread and plantar flexion due to the lack of flexor muscle activity.

Functional assessment of the animals' gait was performed at one week post-surgery and then every two weeks after until 90 days post-surgery to determine the functional status of the tibial nerve in rats. (See Bain et al., Plast. Reconstr. Surg. (1989) 83:129-138, the entire disclosure of which is herein incorporated by reference for all purposes). The rat's hind feet were pressed on an inkpad before walking along an 8×52 cm track ("walking track data"). Measurements were taken from the strip and applied to the following formula:

TFI=−37.2((EPL−NPL)/NPL)+104.4((ETS−NTS)/NTS)+45.6((EIT−NIT)/NIT)−8.8, where "E" is the treatment or treated paw, "N" is the normal or untreated paw, "PL" is the print length, "TS" is the toe spread, and "IT" is the intermediary toe spread.

Figure 2:
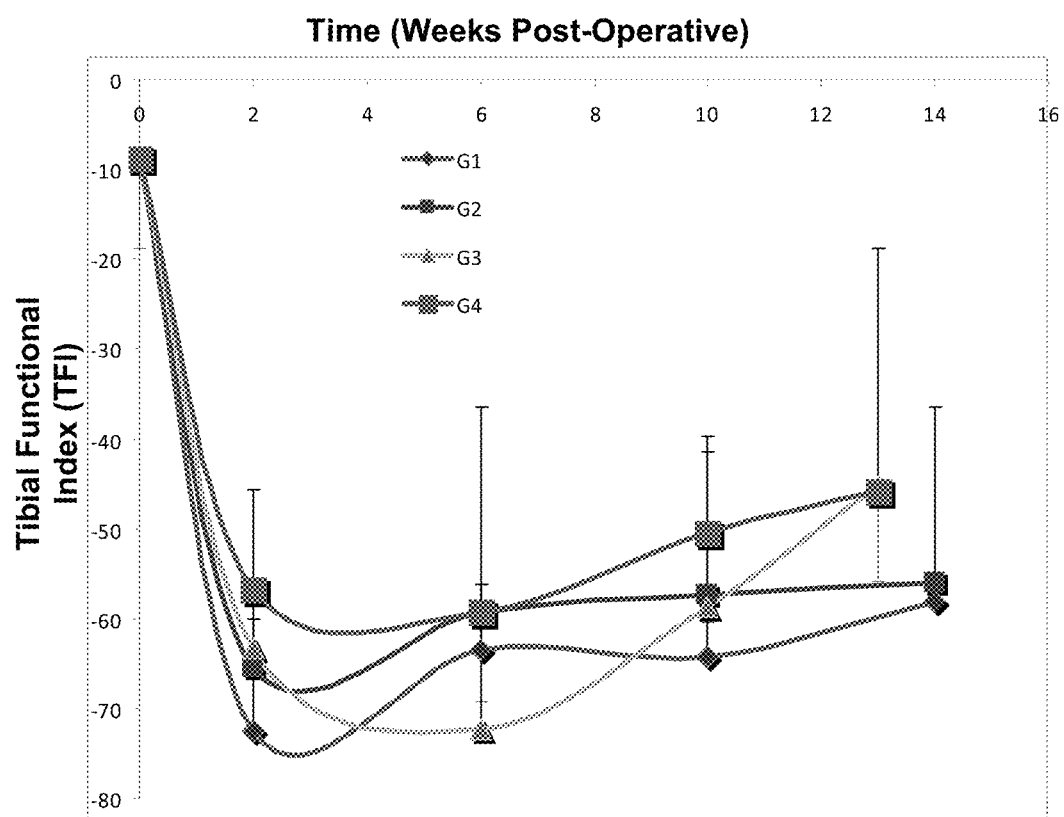
FIG. 2 is a graph showing the average Tibial Functional Index (TFI) for the rats in each of treatment groups G1, G2, G3 and G4 as a function of time in weeks after surgery (Post Operative Week), where t=0 is the TFI measured before surgery.
Figure 3A:
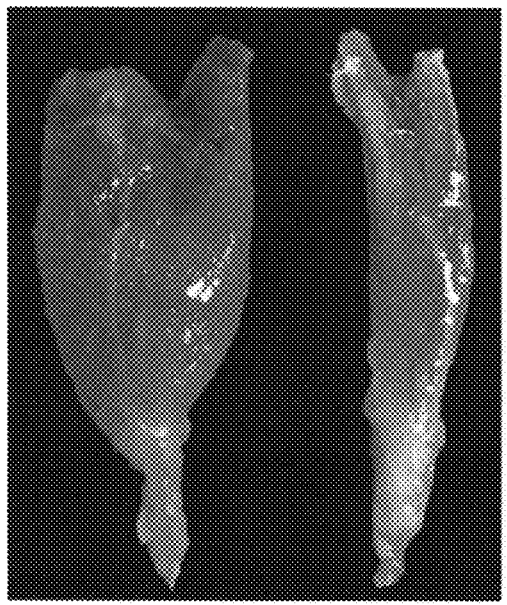
FIG. 3 is a series of photographs showing representative gastrocnemius muscles harvested from the contralateral control leg (muscle shown on the left side of each panel) and treated leg (muscle shown on the right side of each panel) of a rat for each of the G1 (FIG. 3A), G2 (FIG. 3B), G3 (FIG. 3C) and G4 (FIG. 3D) treatment groups.
Figure 3B:
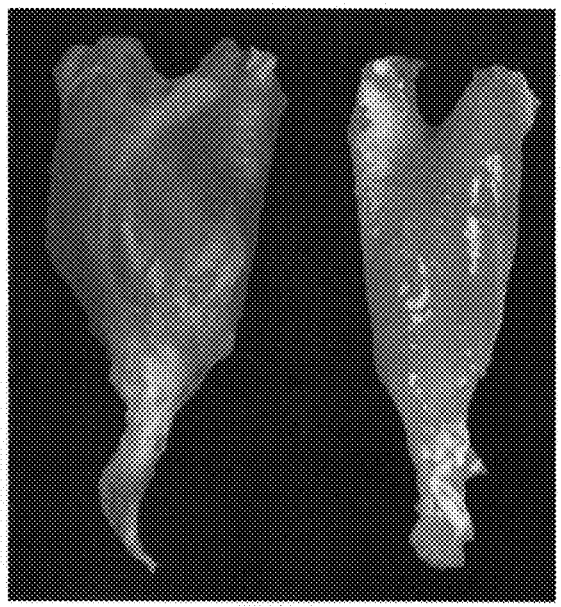
Figure 3C:
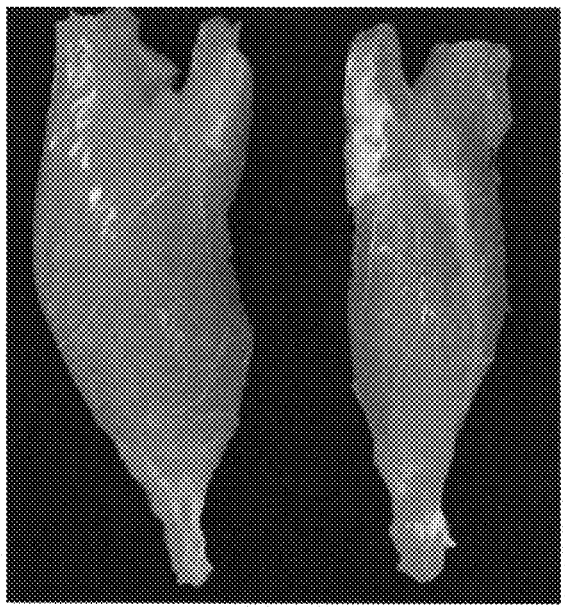
Figure 3D:
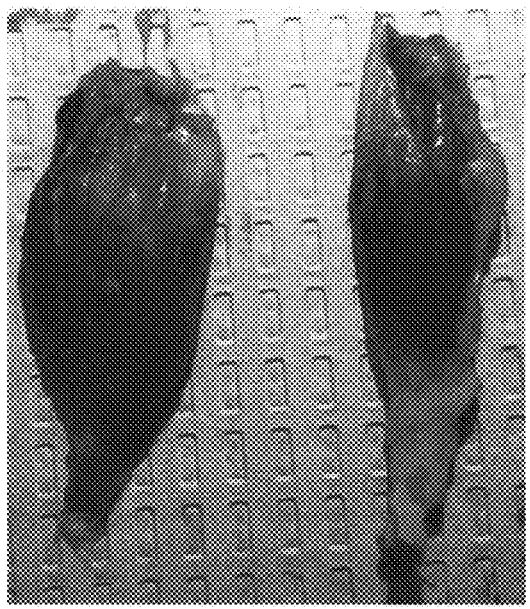

As shown in FIG. 2, there was significant improvement in the TFI over time for the rats that were treated with side-to-side neurorrhaphy. Specifically, the TFI of the G3 and G4 rats improved at a much faster rate than the G1 and G2 rats, which showed little improvement after about 4 weeks post-operative. The faster rate of improvement in the G3 and G4 rats indicates that side-to-side neurorrhaphy using a bridging element at least partially inhibits atrophy of the denervated gastrocnemius muscle.

Example 3

Nerves and Conduit Tissue Sampling

At 90 days post-surgery, animals were killed by $CO_2$ inhalation. The sciatic, tibial, and peroneal nerves were harvested and weighed along with the collagen conduits and the entire gastrocnemius muscle for histologic analysis to generate G1, G2, G3 and G4 samples. A 0.5 cm segment of the distal segment of the tibial nerve was harvested for histological analysis. Tissue from the contralateral hind-limbs was used as controls and harvested at the same time. The nerve tissue was embedded in paraffin, sectioned at 3 μm, mounted on slides and stained with hematoxilyn (Fisher Scientific) and eosin (Thermo Scientific) ("H and E"). The conduit was embedded in paraffin and prepared as described below for PGP 9.5 Immunohistochemistry staining.

Example 4

Muscle Tissue Sampling Tissue

The entire gastrocnemius muscle was harvested from each rat at the same time as the nervous tissue harvesting, weighed and then fixed in 10% buffered formalin (FIG. 3). FIG. 3 shows representative muscles taken from control and treated legs of a rat for G1 (FIG. 3A), G2 (FIG. 3B), G3 (FIG. 3C) and G4 (FIG. 3D). A central 5 mm cross-section of the muscle was dehydrated, embedded in paraffin, cut at 3 μm, and stained with hematoxilyn and eosin (not shown). The stained samples were examined under light microscopy. Groups were compared by an ANOVA or t-test with a=0.05.

Figure 4:
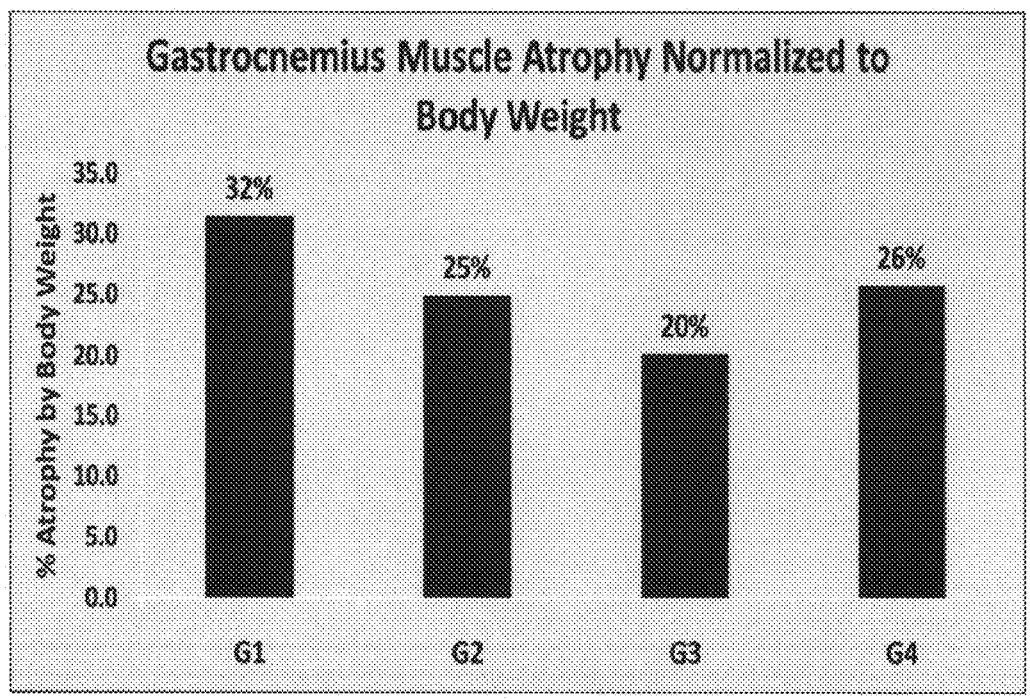
FIG. 4 is a bar chart showing the percentage of gastrocnemius muscle atrophy of each treatment group G1, G2, G3 and G4 as determined by comparing the treated gastrocnemius muscle weight with the control (i.e., contralateral) gastrocnemius muscle weight and normalizing the percent change in gastrocnemius weight to the rat total body weight.

The treatment gastrocnemius muscle weight was compared to the contralateral gastrocnemius and normalized to each rat's body weight. As shown in FIG. 4, the G3 rats demonstrated the least amount of muscle atrophy (20±2.6%) compared to the G1 rats (32±14%), G2 rats (25±7.6%) and G4 rats (26±3.0%). A statistically significant difference was seen between the G3 rats and the G1 rats (p=0.03), but not for the G3 rats and the G2 rats (p=0.11), which indicates that side-to-side neurorrhaphy using a bridging element at least partially inhibits atrophy of the gastrocnemius muscle.

Example 5

PGP 9.5 Immunohistochemistry Staining

Paraffin embedded collagen conduit was cut into sections 3-4 microns thick on positively charged slides. Slides were air-dried, treated with xylene and melted in a 60° C. oven for 30 minutes. Slides were placed on the BenchMark XT (Ventana Medical Systems, Tucson, Ariz.) autostainer and de-paraffinized with EZ Prep solution (Ventana Medical Systems). Slides pre-treatment was performed with CC1 (Ventana Medical Systems) for 60 minutes. Anti-PGP 9.5 antibody (Dako, Carpinteria, Calif., catalog #Z5116) was applied at a dilution of 1:500 for 2 hours at 37° C. Detection was performed using the IView DAB detection kit (Ventana Medical Systems). Secondary antibody (Sigma, anti-rabbit at a 1:100 dilution) was applied for 32 minutes. Slides were counterstained with hematoxylin for 4 minutes. Slides were removed from the autostainer and placed in a mixture of DAWN®/dH2O, Slides were washed in DAWN®/dH2O, Slides were de-hydrated in graded alcohols (70%×1, 95%×2 and 100%×2) 30 seconds each and cover slipped.

Figure 5:
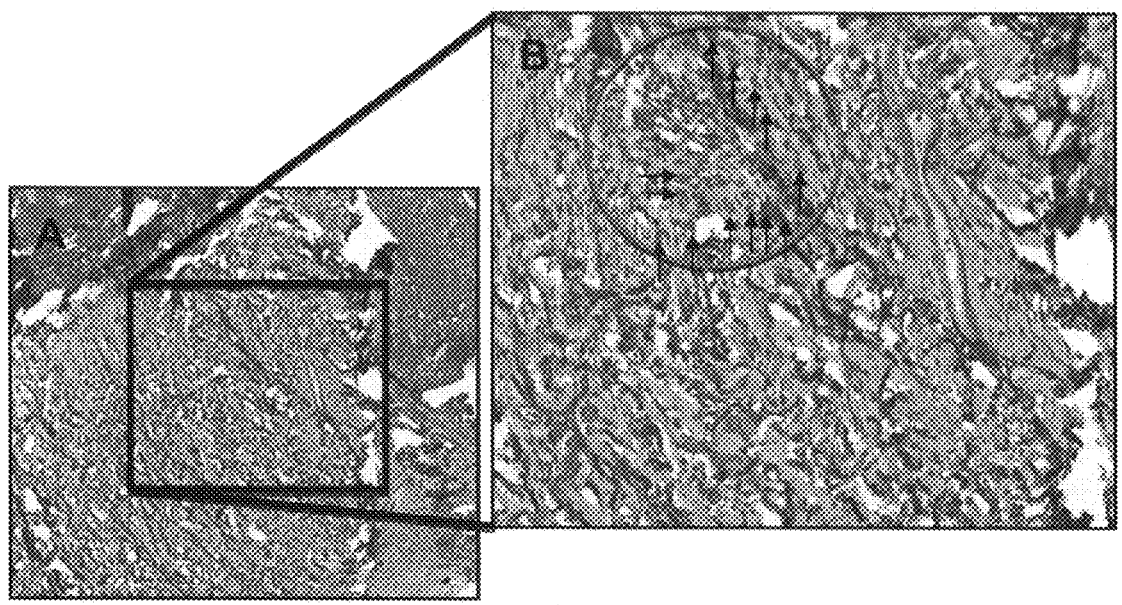
FIG. 5A is a histological section of a collagen bridging element (or conduit) from a G3 rat stained with PGP 9.5, where axons are shown in red.
FIG. 5B shows an enhanced section with a red ring indicating an area with axonal sprouting through the conduit, and arrows pointing to representative axons.

As shown in FIG. 5, the histology of the conduit sections showed evidence of neural sprouts/growth through the conduit in 5 out of 8 slide samples. FIG. 5A shows a cross section of the collagen conduit, taken from a G3 rat stained with PGP 9.5 demonstrating neuronal sprouting through the conduit. FIG. 5B shows an expanded section of FIG. 5A, with a red ring surrounding an area of neuronal sprouting through the conduit. Arrows indicate many of the representative axonal growths that were stained by PGP 9.5. This shows that axonal growth surprisingly and unexpectedly occurs within a bridging element used for side-to-side neurorrhaphy.

Example 6

Whole Slide Imaging and Image Analysis for Determining Nuclei Concentration

The H and E stained muscle, nerves and conduit slides, as prepared above, were digitally scanned with the ScanScope® XT system (Aperio Inc., Vista, Calif., USA). The conduit and selected nerves cross section tissue slides were de-stained and then stained with PGP 9.5 to highlight nerves and nerve sprouts. ImageScope analysis algorithms (Aperio Inc., Vista, Calif., USA) were used for image analysis. (See Teman et al. Leukemia Research (2010) 34:871-876, the entire disclosure of which is herein incorporated by reference for all purposes).

A nuclear image analysis algorithm was used for enumeration of nuclei in both muscle and nerve tissue. Positive pixel count algorithm was utilized to calculate the total tissue area of interest where nuclei were counted. Analysis was performed on entire tissue section represented on the slides, however, areas of staining or tissue artifacts and blood vessels were excluded using a negative pen tool. Nuclei were presented as a ratio to the total area defined by positive pixel count. For muscle tissue, the number of nuclei represented as a ratio to total area of analysis was used for comparison between the various treatment groups. Similarly, the number of nuclei as a ratio of nerve tissue area was used for the comparison between different groups.

Figure 6:
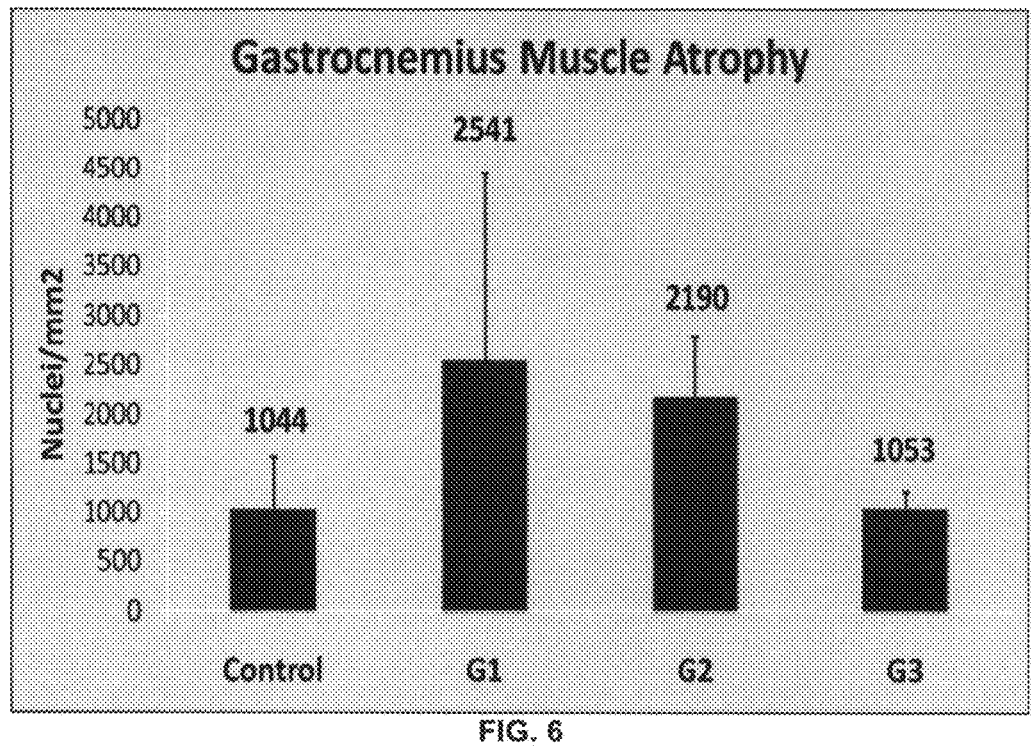
FIG. 6 is a bar chart showing the average gastrocnemius muscle atrophy of G1, G2 and G3 treatment groups compared to control samples as represented by the nuclei concentration (nuclei/mm$^2$) measured in central cross sections of the gastrocnemius muscle for each sample.

The average nuclei concentration in the cross section of the gastrocnemius muscle (as measured by nuclei/mm$^2$) in the G3 samples, which had a 0.24% change in gastrocnemius muscle weight, were similar to the average nuclei concentration number in the control tissue. In contrast, both G1 and G2 samples showed a large increase in the number of nuclei/mm$^2$ (58.91% and 52.33% change respectively), as shown in FIG. 6. The increased number of nuclei/mm$^2$ in the G1 and G2 samples indicates that the gastrocnemius muscle atrophied. In contrast, the results indicated that there was little to no muscle atrophy in the G3 sample, and that side-to-side neurorrhaphy using a bridging element at least partially inhibits atrophy of the gastrocnemius muscle.

Figure 7:
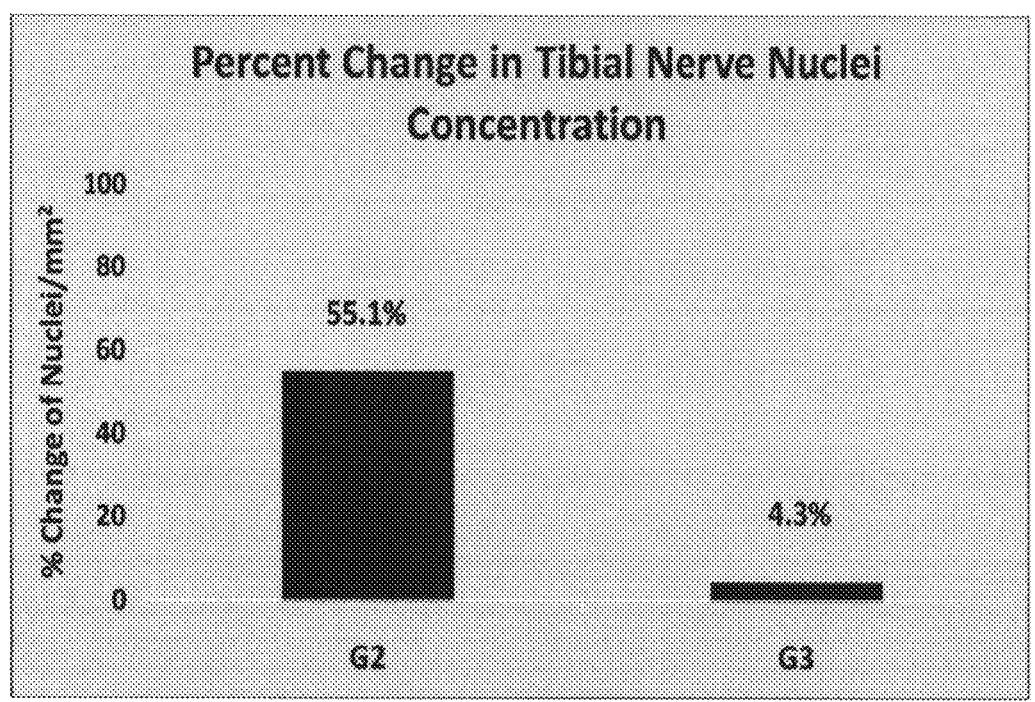
FIG. 7 is a bar chart showing the tibial nerve nuclei percent change in the G2 and G3 treatment groups represented by the % change in the nuclei concentration (nuclei/mm$^2$) between the proximal and distal segments of the tibial nerve.

As shown in FIG. 7, the proportion of tibial nerve nuclei/mm$^2$ in the cross section of the G2 distal segment of the tibial nerve was 55.1% greater than in the cross section of the G2 proximal segment of the tibial nerve. This indicates inflammation and proliferation in the distal segment of the tibial nerve consistent with denervation (i.e., nerve injury). In contrast, the proportion of tibial nerve nuclei/mm$^2$ in the cross section of the G3 distal segment of the tibial nerve was 4.3% greater than in the cross section of the G3 proximal segment of the tibial nerve, indicating that side-to-side neurorrhaphy using a bridging element inhibits atrophy of and/or maintains the viability of the tibial nerve.

Thus, this disclosure provides, among other things, methods for repairing nerve injuries that include performing side-to-side neurorrhaphy using a bridging element between a first epineurial window on a donor nerve and a second epineurial window on a recipient nerve. Various features and advantages of the invention are set forth in the claims.

REFERENCES

The following references are herein incorporated by reference in their entireties for all purposes:

1. Alluin O, Wittmann C, Marqueste T, Chabas J F, Garcia S, Lavaut M N, Guinard D, Feron F, Decherchi P. Functional recovery after peripheral nerve injury and implantation of a collagen guide. Biomaterials. 2009 January; 30(3):363-73. [Epub 2008 Oct. 16.]
2. Amr S M, Essam A M, Abdel-Meguid A M, Kholeif A M, Moharram A N, El-Sadek R E. Direct cord implantation in brachial plexus avulsions: revised technique using a single stage combined anterior (first) posterior (second) approach and end-to-side side-to-side grafting neurorrhaphy. J Brachial Plex Peripher Nerve Inj. 2009 June; 4:8.
3. Amr S M, Moharram A N. Repair of brachial plexus lesions by end-to-side side-to-side grafting neurorrhaphy: experience based on 11 cases. Microsurgery. 2005; 25(2):126-46.
4. Arai T, Nakao Y, Sugiki T, Tochigi H, Okuyama N. Side-to-side neurorrhaphy in sciatic nerves of rat. J Japanese Soc Surg Hand. 2001; 18(2):155-158.
5. Archibald S J, Krarup C, Shefner J, Li S T, Madison R D. A collagen-based nerve guide conduit for peripheral nerve repair: an electrophysiological study of nerve regeneration in rodents and nonhuman primates. J Comp Neurol. 1991 April; 306(4):685-96.
6. Archibald, S J, Krarup, C, Madison, R D. Factors that influence peripheral nerve regeneration: electrophysiological study of the monkey median nerve. Ann Neurol. 2002; 51(1):69-81.
7. Archibald, S J, Krarup, C, Shefner, J, Li, S T, Madison, R D. Collagen-based nerve guide conduit for peripheral nerve repair: an electrophysiological study of nerve regeneration in rodents and non-human primates. J. Comp. Neurol. 1991; 306(4):685-696.
8. Archibald, S J, Shefner, J, Krarup, C, Madison, R D. Monkey median nerve repaired by nerve graft or collagen nerve guide tube. J. Neurosci. 1995; 15(5):4109-4123.
9. Bain J R, Mackinnon S E, Hunter D A. Functional evaluation of complete sciatic, peroneal, and posterior tibial nerve lesions in the rat. Plast Reconstr Surg. 1989; 83:129-138.
10. Benito-Ruiz J, Navarro-Monzonis A, Piqueras A, Baena-Montilla P. Invaginated vein graft as nerve conduit: an experimental study. Microsurgery. 1994; 15(2):105-15.
11. Berger A, Lassner F, Schaller E. [The Dellon tube in injuries of peripheral nerves]. Handchir Mikrochir Plast Chir. 1994 January; 26(1):44-7.
12. Bertleff M J, Meek M F, Nicolai J P. A prospective clinical evaluation of biodegradable neurolac nerve guides for sensory nerve repair in the hand. J Hand Surg Am. 2005 May; 30(3):513-8.
13. Biers S M, Brading A F. Nerve regeneration: might this be the only solution for functional problems of the urinary tract? Curr Opin Urol. 2003 November; 13(6):495-500.
14. Burnett M G, Zager E L. Pathophysiology of peripheral nerve injury: a brief review. Neurosurg Focus. 2004 May; 16(5):E1.
15. Chen Z, Hong G, Wang F, et al. Comparison of the nerve regeneration of end-to-side neurorrhaphy and side-to-side neurorrhaphy: an experimental study. Chinese Journal of Practical Hand Surgery. 2001-01.
16. Clavijo-Alvarez J A, Nguyen V T, Santiago L Y, Doctor J S, Andrew Lee W P, Marra K G. Comparison of biodegradable conduits within aged rat sciatic nerve defects. Plast Reconstr Surg. 2007 May; 119(6): 1839-1851.
17. Cui T, Yan Y, Zhang R, Liu L, Xu W, Wang X. Rapid prototyping of a double-layer polyurethane-collagen conduit for peripheral nerve regeneration. Tissue Eng Part C Methods. 2009 March; 15(1):1-9.
18. de Ruiter G C, Malessy M J, Yaszemski M J, Windebank A J, Spinner R J. Designing ideal conduits for peripheral nerve repair. Neurosurg Focus. 2009 February; 26(2):E5.
19. Deumens R, Bozkurt A, Meek M F, Marcus M A, Joosten E A, Weis J, Brook G A. Repairing injured peripheral nerves: Bridging the gap. Prog Neurobiol. 2010 November; 92(3):245-76. [Epub 2010 Oct. 13.]
20. Fabre T, Schappacher M, Bareille R, Dupuy B, Soum A, Bertrand-Barat J, Baquey C. Study of a (trimethylenecarbonate-co-epsilon-caprolactone) polymer—part 2: in vitro cytocompatibility analysis and in vivo ED1 cell response of a new nerve guide. Biomaterials. 2001 November; 22(22):2951-8.
21. Gatta R. Sulla anastomosi latero-terminale dei tronchi nervosa. Archivio Italiano Chirurgia. 1938; 48:155-171.
22. Hayashi A, Pannucci C, Moradzadeh A, Kawamura D, Magill C, Hunter D A, Tong A Y, Parsadanian A, Mackinnon S E, Myckatyn T M. Axotomy or compression is required for axonal sprouting following end-to-side neurorrhaphy. Exp Neurol. 2008 June; 211(2):539-50. [Epub 2008 Mar. 25.]
23. Hobson M I. Increased vascularisation enhances axonal regeneration within an acellular nerve conduit. Ann R Coll Surg Engl. 2002 January; 84(1):47-53.
24. Ichihara S, Inada Y, Nakada A, Endo K, Azuma T, Nakai R, Tsutsumi S, Kurosawa H, Nakamura T. Development of new nerve guide tube for repair of long nerve defects. Tissue Eng Part C Methods. 2009 September; 15(3):387-402.
25. Itoh S, Takakuda K, Kawabata S, Aso Y, Kasai K, Itoh H, Shinomiya K. Evaluation of cross-linking procedures of collagen tubes used in peripheral nerve repair. Biomaterials. 2002 December; 23(23):4475-81.
26. Jansen K, Meek M F, van der Werff J F, van Wachem P B, van Luyn M J. Long-term regeneration of the rat sciatic nerve through a biodegradable poly(DL-lactide-epsilon-caprolactone) nerve guide: tissue reactions with focus on collagen III/IV reformation. J Biomed Mater Res A. 2004 May; 69(2):334-41.
27. Jansen K, Meek M F, van der Werff J F, van Wachem P B, van Luyn M J. Long-term regeneration of the rat sciatic nerve through a biodegradable poly(DL-lactide-epsilon-caprolactone) nerve guide: tissue reactions with focus on collagen III/IV reformation [Erratum]. J Biomed Mater Res A. 2006 May; 77(2):436.
28. Jansen K, van der Werff J F, van Wachem P B, Nicolai J P, de Leij L F, van Luyn M J. A hyaluronan-based nerve guide: in vitro cytotoxicity, subcutaneous tissue reactions, and degradation in the rat. Biomaterials. 2004 February; 25(3):483-9.
29. Jeans L A, Gilchrist T, Healy D. Peripheral nerve repair by means of a flexible biodegradable glass fibre wrap: a comparison with microsurgical epineurial repair. J Plast Reconstr Aesthet Surg. 2007; 60(12):1302-8. [Epub 2007 Mar. 9.]
30. Jung J M, Chung M S, Kim M B, Baek G H. Contribution of the proximal nerve stump in end-to-end nerve repair: In a rat model. Clin Orthop Surg. 2009; 1:90-95.
31. Kalbermatten D F, Pettersson J, Kingham P J, Pierer G, Wiberg M, Terenghi G. New fibrin conduit for peripheral nerve repair. J Reconstr Microsurg. 2009 January; 25(1):27-33. [Epub 2008 Oct. 16.]
32. Kitahara A K, Nishimura Y, Shimizu Y, Endo K. Facial nerve repair accomplished by the interposition of a collagen nerve guide. J. Neurosurg. 2000 July; 93(1):113-20.
33. Kitahara A K, Suzuki Y, Qi P, Nishimura Y, Suzuki K, Kiyotani T, Takimoto Y, Nakamura T, Shimizu Y, Endo K. Facial nerve repair using a collagen conduit in cats. Scand J Plast Reconstr Surg Hand Surg. 1999 June; 33(2):187-93.
34. Li S T, Archibald S J, Krarup C, Madison R D. Peripheral nerve repair with collagen conduits. Clin Mater. 1992; 9(3-4):195-200.
35. Liu B S. Fabrication and evaluation of a biodegradable proanthocyanidin-crosslinked gelatin conduit in peripheral nerve repair. J Biomed Mater Res A. 2008 December; 87(4):1092-102.
36. Ljungberg C, Johansson-Ruden G, Boström K J, Novikov L, Wiberg M. Neuronal survival using a resorbable synthetic conduit as an alternative to primary nerve repair. Microsurgery. 1999; 19(6):259-64.
37. Lundborg, G. Nerve Injury and Repair. New York: Churchill Livingstone. 1988.
38. Mackinnon S E, Doolabh V B, Novak C B, Trulock E P. Clinical outcome following nerve allograft transplantation. Plast Reconstr Surg. 2001; 107:1419-1429.
39. Mackinnon, S E, Dellon, A L, Hudson, A R, Hunter, D A. A primate model for chronic nerve compression. J Reconstr Microsurg. 1985; 1:185-194.
40. Magdi Sherif M, Amr A H. Intrinsic hand muscle reinnervation by median-ulnar end-to-side bridge nerve graft: Case report. J Hand Surg. 2010; 35A:446-450.
41. Matsumoto K, Ohnishi K, Kiyotani T, Sekine T, Ueda H, Nakamura T, Endo K, Shimizu Y. Peripheral nerve regeneration across an 80-mm gap bridged by a polyglycolic acid (PGA)-collagen tube filled with laminin-coated collagen fibers: a histological and electrophysiological evaluation of regenerated nerves. Brain Res. 2000 June; 868(2):315-28.
42. Meek M F, Coert J H. US Food and Drug Administration/Conformit Europe-approved absorbable nerve conduits for clinical repair of peripheral and cranial nerves. Ann Plast Surg. 2008 April; 60(4):466-72.
43. Meek M F, Nicolai J P, Robinson P H. Secondary digital nerve repair in the foot with resorbable p(DLLA-epsilon-CL) nerve conduits. J Reconstr Microsurg. 2006 April; 22(3):149-51.
44. Meyer R S, Abrams R A, Botte M J, Davey J P, Bodine-Fowler S C. Functional recovery following neurorrhaphy of the rat sciatic nerve by epineurial repair compared with tubulization. J Orthop Res. 1997 September; 15(5):664-9.
45. Myckatyn T M, MacKinnon S E. Microsurgical repair of peripheral nerves and nerve grafts. Grabb and Smith's Plastic Surgery, 6th Ed. (2007).
46. Navarro X, Rodriguez F J, Ceballos D, Verdu E. Engineering an artificial nerve graft for the repair of severe nerve injuries. Med Biol Eng Comput. 2003 March; 41(2):220-6.
47. Nectow A, Marra K, Kaplan D L. Biomaterials for the development of peripheral nerve guidance conduits. Tissue Eng Part B Rev. 2011 August; [Epub ahead of print]
48. Okamoto H, Hata K, Kagami H, Okada K, Ito Y, Narita Y, Hirata H, Sekiya I, Otsuka T, Ueda M. Recovery process of sciatic nerve defect with novel bioabsorbable collagen tubes packed with collagen filaments in dogs. J Biomed Mater Res A. 2010 March; 92(3):859-68.
49. O'Neill A C, Randolph M A, Bujold K E, Kochevar I E, Redmond R W, Winograd J M. Preparation and integration of human amnion nerve conduits using a light-activated technique. Plast Reconstr Surg. 2009 August; 124(2):428-37.
50. Papalia I, Geuna S, D'Alcontres F S, Tos P. Origin and history of end-to-side neurorrhaphy. Microsurgery. 2007; 27(1):56-61.
51. Patel M, Mao L, Wu B, Vandevord P J. GDNF-chitosan blended nerve guides: a functional study. J Tissue Eng Regen Med. 2007 September-October; 1(5):360-7.
52. Patel M, VandeVord P J, Matthew H W, De Silva S, Wu B, Wooley P H. Collagen-chitosan nerve guides for peripheral nerve repair: a histomorphometric study. J Biomater Appl. 2008 September; 23(2):101-21. [Epub 2008 May 8.]

53. Ray W Z, Mackinnon S E. Management of nerve gaps: Autografts, allografts, nerve transfers, and end-to-side neurorrhaphy. Exp Neurol. 2010 May; 223(1):77-85. [Epub 2009 Apr. 5.]
54. Smith R M, Wiedl C, Chubb P, Greene C H. Role of small intestine submucosa (SIS) as a nerve conduit: preliminary report. J Invest Surg. 2004 November-December; 17(6): 339-44.
55. Spyropoulou G A, Lykoudis E G, Batistatou A, Papalois A E, Tagaris G, Pikoulis E, Bastounis E, Papadopoulos O. New pure motor nerve experimental model for the comparative study between end-to-end and end-to-side neurorrhaphy in free muscle flap neurotization. J Reconstr Microsurg. 2007; 23(7):391-398.
56. Stevenson T R, Kadhiresan V A, Faulkner J A. Tubular nerve guide and epineurial repair: comparison of techniques for neurorrhaphy. J Reconstr Microsurg. 1994 May; 10(3):171-4.
57. Sun M, McGowan M, Kingham P J, Terenghi G, Downes S, Novel thin-walled nerve conduit with microgrooved surface patterns for enhanced peripheral nerve repair. J Mater Sci Mater Med. 2010 October; 21(10):2765-74. [Epub 2010 Sep. 28.]
58. Taras J S, Jacoby S M. Repair of lacerated peripheral nerves with nerve conduits. Tech Hand Up Extrem Surg. 2008 June; 12(2):100-6.
59. Taras J S, Nanavati V, Steelman P. Nerve conduits. J Hand Ther. 2005 April-June; 18(2): 191-7.
60. Teman C J, Wilson A R, Perkins S L, Hickman K, Prchal J T, Salama M E. Quantification of fibrosis and osteosclerosis in myeloproliferative neoplasms: a computer-assisted image study. Leuk Res. 2010; 34:871-876.
61. Terzis J K, Tzafetta K. The "Babysitter" procedure: minihypoglossal to facial nerve transfer and cross facial nerve grafting. Plas Reconstr Surg. 2009; 123(3):865-876.
62. Tham S K, Morrison W A. Motor collateral sprouting through an end-to-side nerve repair. J Hand Surg. 1998 September; 23(5):844-851.
63. Ulkur E, Karagoz H, Celikoz B, Turan P, Arbak S, Yapar M. Nerve graft prefabrication: preliminary study. J Reconstr Microsurg. 2008 April; 24(2):137-135.
64. Vasconcelos B C, Gay-Escoda C. Facial nerve repair with expanded polytetrafluoroethylene and collagen conduits: an experimental study in the rabbit. J Oral Maxillofac Surg. 2000 November; 58(11):1257-62.
65. Viterbo F, Trindade J C, Hoshino K, Neto A M. End-to-side Neurorrhaphy with removal of the epineurial sheath: an experimental study in rats. Plast Reconstr Surg. 1994 December; 94(7):1038-1047.
66. Wangensteen K J, Kalliainen L K. Collagen tube conduits in peripheral nerve repair: A retrospective analysis. Hand (N Y). 2009 Nov. 24. [Epub ahead of print]
67. Watanabe K, Tsukagoshi T, Kuroda M, Hosaka Y. Nerve conduit using fascia-wrapped fibrocollagenous tube. J Reconstr Microsurg. 2001 July; 17(5):363-8.
68. Whitworth I H, Brown R A, Doré C, Green C J, Terenghi G. Orientated mats of fibronectin as a conduit material for use in peripheral nerve repair. J Hand Surg Br. 1995 August; 20(4):429-36.
69. Xiu X L, Zhang S C, Wang J B, et al. An experimental study of the side-to-side neurorrhaphy to repair incomplete injury of peripheral nerve. The Orthopedic Journal of China. 2001-10.
70. Yang Y C, Shen C C, Huang T B, Chang S H, Cheng H C, Liu B S. Characteristics and biocompatibility of a biodegradable genipin-cross-linked gelatin/β-tricalcium phosphate reinforced nerve guide conduit. J Biomed Mater Res B Appl Biomater. 2010 October; 95(1):207-17.
71. Yao L, de Ruiter G C, Wang H, Knight A M, Spinner R J, Yaszemski M J, Windebank A J, Pandit A. Controlling dispersion of axonal regeneration using a multichannel collagen nerve conduit. Biomaterials. 2010 August; 31(22):5789-97. [Epub 2010 Apr. 28.]
72. Yoshitatsu S, Matsuda K, Yano K, Hosokawa K, Tomita K. Muscle flap mass preservation by sensory reinnervation with end-to-side neurorrhaphy: an experimental study in rats. J Reconstr Microsurg. 2008 September; 24(7):479-487.
73. Yüksel F, Karacaoğlu E, Güler M M. Nerve regeneration through side-to-side neurorrhaphy sites in a rat model: a new concept in peripheral nerve surgery. Plast Reconstr Surg. 1999 December; 104(7):2092-9.
74. Yüksel F, Peker F, Celiköz B. Two applications of end-to-side nerve neurorrhaphy in severe upper-extremity nerve injuries. Microsurgery. 2004; 24(5):363-8.
75. Yüksel F, Ulkür E, Baloğlu H, Celikoz B. Nerve regeneration through a healthy peripheral nerve trunk as a nerve conduit: a preliminary study of a new concept in peripheral nerve surgery. Microsurgery. 2002; 22(4):138-43.
76. Zukor K, He Z. Regenerative medicine: Drawing breath after spinal injury. Nature. 2011; 475:177-178.
77. Australian Patent Publication Number AU2006329152
78. Canadian Patent Publication Number CA2078982
79. Canadian Patent Publication Number CA2628720
80. Canadian Patent Publication Number CA2634351
81. Canadian Patent Publication Number CA2713214
82. Canadian Patent Publication Number CA2713214
83. Chinese Patent Publication Number CN100479785
84. Chinese Patent Publication Number CN100560037
85. Chinese Patent Publication Number CN101138656
86. Chinese Patent Publication Number CN101474423
87. Chinese Patent Publication Number CN101474424
88. Chinese Patent Publication Number CN101507842
89. Chinese Patent Publication Number CN101543645
90. Chinese Patent Publication Number CN101564552
91. Chinese Patent Publication Number CN101579246
92. Chinese Patent Publication Number CN101711893
93. Chinese Patent Publication Number CN1380115
94. Chinese Patent Publication Number CN1843307
95. Chinese Patent Publication Number CN201230913
96. European Patent Publication Number EP0261833
97. European Patent Publication Number EP0534152
98. European Patent Publication Number EP0534152
99. European Patent Publication Number EP1163019
100. European Patent Publication Number EP1163019
101. European Patent Publication Number EP1201256
102. European Patent Publication Number EP1201256
103. European Patent Publication Number EP1443983
104. European Patent Publication Number EP1443983
105. European Patent Publication Number EP1650224
106. European Patent Publication Number EP1867348
107. European Patent Publication Number EP1867348
108. European Patent Publication Number EP1878451
109. European Patent Publication Number EP1948263
110. European Patent Publication Number EP1968661
111. European Patent Publication Number EP1968661
112. European Patent Publication Number EP1968661
113. European Patent Publication Number EP2240090
114. British Patent Publication Number GB0224776
115. Japanese Patent Publication Number JP2004208808
116. Korean Patent Publication Number KR100700674
117. Korean Patent Publication Number KR100718073
118. Korean Patent Publication Number KR20030087196

119. Korean Patent Publication Number KR20050095250
120. Korean Patent Publication Number KR20060006295
121. Korean Patent Publication Number KR20060018752
122. Korean Patent Publication Number KR20080072656
123. Korean Patent Publication Number KR20090064617
124. Mexican Patent Publication Number MX2008006463
125. Singapore Patent Publication Number SG125885
126. Taiwanese Patent Publication Number TW287459
127. Ukraine Patent Publication Number UA9421
128. PCT Patent Publication Number WO 1988/006866
129. PCT Patent Publication Number WO 2000/051662
130. PCT Patent Publication Number WO 2000/056376
131. PCT Patent Publication Number WO 2000/056376
132. PCT Patent Publication Number WO 2002/047557
133. PCT Patent Publication Number WO 2002/047757
134. PCT Patent Publication Number WO 2003/041758
135. PCT Patent Publication Number WO 2003/041758
136. PCT Patent Publication Number WO 2003/041758
137. PCT Patent Publication Number WO 2004/101002
138. PCT Patent Publication Number WO 2005/020825
139. PCT Patent Publication Number WO 2005/020825
140. PCT Patent Publication Number WO 2005/020825
141. PCT Patent Publication Number WO 2005/037070
142. PCT Patent Publication Number WO 2007/057177
143. PCT Patent Publication Number WO 2007/057177
144. PCT Patent Publication Number WO 2007/071167
145. PCT Patent Publication Number WO 2007/092417
146. PCT Patent Publication Number WO 2007/142579
147. PCT Patent Publication Number WO 2008/070428
148. PCT Patent Publication Number WO 2008/121331
149. PCT Patent Publication Number WO 2008/140413
150. PCT Patent Publication Number WO 2008/144514
151. PCT Patent Publication Number WO 2009/085823
152. PCT Patent Publication Number WO 2009/094225
153. PCT Patent Publication Number WO 2009/094225
154. PCT Patent Publication Number WO 2009/094225
155. PCT Patent Publication Number WO 2009/094225
156. PCT Patent Publication Number WO 2009/117127
157. PCT Patent Publication Number WO 2009/117127
158. PCT Patent Publication Number WO 2010/042207
159. U.S. Patent Application Publication Number 2002/086047
160. U.S. Patent Application Publication Number 2002/156150
161. U.S. Patent Application Publication Number 2002/173558
162. U.S. Patent Application Publication Number 2003/060836
163. U.S. Patent Application Publication Number 2003/072749
164. U.S. Patent Application Publication Number 2004/122454
165. U.S. Patent Application Publication Number 2004/234576
166. U.S. Patent Application Publication Number 2005/069525
167. U.S. Patent Application Publication Number 2006/018947
168. U.S. Patent Application Publication Number 2007/067883
169. U.S. Patent Application Publication Number 2007/135929
170. U.S. Patent Application Publication Number 2007/141166
171. U.S. Patent Application Publication Number 2007/182041
172. U.S. Patent Application Publication Number 2008/051490
173. U.S. Patent Application Publication Number 2008/095823
174. U.S. Patent Application Publication Number 2008/132602
175. U.S. Patent Application Publication Number 2009/024150
176. U.S. Patent Application Publication Number 2009/099580
177. U.S. Patent Application Publication Number 2010/0047310
178. U.S. Patent Application Publication Number 2010/0055148
179. U.S. Patent Application Publication Number 2010/0076465
180. U.S. Patent Application Publication Number 2010/0094318
181. U.S. Patent Application Publication Number 2010/0168625
182. U.S. Patent Application Publication Number 2010/0168720
183. U.S. Patent Application Publication Number 2010/0168870
184. U.S. Pat. No. 4,662,884
185. U.S. Pat. No. 4,662,884
186. U.S. Pat. No. 4,669,474
187. U.S. Pat. No. 4,759,764
188. U.S. Pat. No. 4,774,967
189. U.S. Pat. No. 4,778,467
190. U.S. Pat. No. 4,778,467
191. U.S. Pat. No. 4,870,966
192. U.S. Pat. No. 4,870,966
193. U.S. Pat. No. 4,883,618
194. U.S. Pat. No. 4,963,146
195. U.S. Pat. No. 4,963,146
196. U.S. Pat. No. 4,986,828
197. U.S. Pat. No. 5,019,087
198. U.S. Pat. No. 5,019,087
199. U.S. Pat. No. 5,354,305
200. U.S. Pat. No. 5,770,417
201. U.S. Pat. No. 6,309,635
202. U.S. Pat. No. 6,448,076
203. U.S. Pat. No. 6,514,515
204. U.S. Pat. No. 6,548,569
205. U.S. Pat. No. 6,676,675
206. U.S. Pat. No. 6,716,225
207. U.S. Pat. No. 6,716,225
208. U.S. Pat. No. 6,821,946
209. U.S. Pat. No. 6,821,946
210. U.S. Pat. No. 6,838,493
211. U.S. Pat. No. 6,840,962
212. U.S. Pat. No. 6,867,247
213. U.S. Pat. No. 6,899,873
214. U.S. Pat. No. 6,953,482
215. U.S. Pat. No. 7,135,040
216. U.S. Pat. No. 7,135,040
217. U.S. Pat. No. 7,179,883
218. U.S. Pat. No. 7,198,799
219. U.S. Pat. No. 7,268,205
220. U.S. Pat. No. 7,553,923
221. U.S. Pat. No. 7,553,923
222. U.S. Pat. No. 7,618,653
223. U.S. Pat. No. 7,785,628

What is claimed is:

1. A method for repairing an at least partially transected nerve, the method comprising providing a donor nerve and a recipient nerve, wherein the recipient nerve is at least partially transected at a proximal site;

creating a first epineurial window in a side of the donor nerve and a second epineurial window in a side of the recipient nerve at a site distal from the proximal site;

arranging the donor nerve and the recipient nerve in a side-by-side fashion with the first and second epineurial windows proximate to one another;

positioning between the first and second epineurial windows a bridging element having first and second ends and defining a conduit; and connecting the first end of the bridging element to the first epineurial window and the second end of the bridging element to the second epineurial window such that the first and second epineurial windows are in fluid communication with each other via the conduit to permit transmission of signals from the donor nerve to the recipient nerve.

2. The method of claim 1, wherein the bridging element comprises an autologous biological tissue.

3. The method of claim 2, wherein the autologous biological tissue includes a non-nerve graft.

4. The method of claim 1, wherein the bridging element comprises a non-autologous biological tissue.

5. The method of claim 4, wherein the non-autologous biological tissue includes at least one of an allogenic tissue or a xenogenic tissue.

6. The method of claim 1, wherein the bridging element comprises a biologically derived material.

7. The method of claim 6, wherein the biologically derived material includes at least one of a fibrous protein, a polysaccharide, and a glycoprotein.

8. The method of claim 6, wherein the biologically derived material includes at least one of collagen, fibrin, extracellular matrix solution, fibronectin, alginate, gelatin, keratin, thrombin and silk.

9. The method of claim 1, wherein the bridging element comprises a synthetic material.

10. The method of claim 9, wherein the synthetic material comprises at least one of silicon, an aliphatic polyester, a poly(phosphoester), a hydrogel, and a poly(acrylonitrile-co-methylacrylate).

11. The method of claim 10, wherein the aliphatic polyester comprises at least one of poly-glycolic acid, poly-(lactic acid), poly-caprolactone, poly-(lactide-coglycolide) copolymer, poly-(L-lactic acid) and poly(3-hydroxybutyric acid).

12. The method of claim 10, wherein the poly(phosphoester) is at least one of poly((bis(hydroxyethy)terephthalate-ethyl phosphoester/terephthaloyl chloride) and polytetrafluoroethylene.

13. The method of claim 10, wherein the hydrogel comprises at least one of poly(2-hydroxyethyl methacrylate) (PHEMA) and a co-polymer of PHEMA and methyl methacrylate.

14. The method of claim 1, wherein upon connecting the first end of the bridging element to the first epineurial window and the second end of the bridging element to the second epineurial window, chemical signals traverse the bridging element via the conduit.

15. The method of claim 14, wherein the chemical signals are growth factors.

16. The method of claim 1, wherein the at least partially transected nerve is completely transected.

17. The method of claim 1, wherein none of the axons in the donor nerve are injured.

18. A method for at least partially inhibiting atrophy of a muscle that has ceased receiving signals from a nerve that has been severed, the method comprising:

creating a first epineurial window in a side of a healthy donor nerve and a second epineurial window in a side of a recipient nerve, wherein the recipient nerve has been severed proximal the epineurial window;

positioning the first and second epineurial windows of the donor nerve and the recipient nerve in a side-by-side fashion with a gap therebetween;

positioning between the first and second epineurial windows a bridging element having first and second ends and defining a conduit; and connecting the first end of the bridging element to the first epineurial window and the second end of the bridging element to the second epineurial window while maintaining the gap between the first and second epineurial windows such that the first and second epineurial windows are in fluid communication with each other via the conduit, and the bridging element permits transmission of signals from the donor nerve to the muscle via the recipient nerve, thereby at least partially inhibiting atrophy of the muscle.

19. A method for repairing peripheral nerve injuries, the method comprising performing a side-to-side neurorraphy using a bridging element between a first epineurial window on a donor nerve and a second epineurial window on a recipient nerve, wherein the bridging element comprises first and second ends and defining a tubular conduit between the first and second ends, and wherein the bridging element bridges and maintains a gap between the first and second epineurial windows such that the first and second epineurial windows are in fluid communication with each other via the tubular conduit to permit transmission of signals from the donor nerve to the recipient nerve.

* * * * *